United States Patent
Tung et al.

(10) Patent No.: US 6,518,467 B2
(45) Date of Patent: Feb. 11, 2003

(54) METHOD OF MAKING HYDROFLUOROCARBONS AND HYDROCHLOROFLUOROCARBONS

(75) Inventors: Hsueh Sung Tung, Getzville, NY (US); Michael Van Der Puy, Amherst, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 09/752,910

(22) Filed: Dec. 29, 2000

(65) Prior Publication Data

US 2002/0087039 A1 Jul. 4, 2002

(51) Int. Cl.⁷ ................................. C07C 17/26
(52) U.S. Cl. .................. 570/171; 570/172; 570/159
(58) Field of Search ............... 570/171, 172, 570/159

(56) References Cited

U.S. PATENT DOCUMENTS

| | | | |
|---|---|---|---|
| 4,950,364 A | | 8/1990 | Wismer |
| 5,099,081 A | | 3/1992 | Bolmer et al. |
| 5,099,082 A | | 3/1992 | Bolmer et al. |
| 5,208,398 A | | 5/1993 | Wismer |
| 5,326,913 A | * | 7/1994 | Aoyama et al. |
| 5,382,720 A | * | 1/1995 | Ikawa et al. ......... 570/171 |
| 5,395,997 A | | 3/1995 | Van Der Puy et al. |
| 5,481,050 A | * | 1/1996 | Van Der Puy |
| 5,608,126 A | * | 3/1997 | Morikawa et al. |
| 5,739,406 A | | 4/1998 | Pennetreau et al. |
| 5,902,914 A | | 5/1999 | Rygas et al. |
| 5,917,098 A | | 6/1999 | Bertocchio et al. |
| 5,955,638 A | | 9/1999 | Schoebrechts et al. |

FOREIGN PATENT DOCUMENTS

| | | |
|---|---|---|
| CA | 2196586 A1 | 2/1997 |
| JP | 06157366 | 11/1992 |
| JP | 08198783 | 1/1995 |
| JP | 11158088 | 9/1998 |
| JP | 11071306 A | 3/1999 |
| WO | WO98/50329 | 12/1998 |
| WO | WO98/50330 | 12/1998 |

* cited by examiner

Primary Examiner—Alan Siegel
(74) Attorney, Agent, or Firm—Colleen Szuch

(57) ABSTRACT

A method of producing hydrofluorocarbons and/or hydrochlorofluorocarbons by using halogenated alkanes as a principal reactant. Generally, the method comprises the step of: (a) reacting a starting halogenated alkane corresponding to the formula (I):

$$H_3C\text{—}CX_3 \quad \text{(I)}$$

wherein X is independently fluorine or chlorine, with a hydrohalocarbon adduct in the presence of a catalyst to form a hydrofluorocarbon and/or hydrochlorofluorocarbon.

26 Claims, No Drawings

METHOD OF MAKING HYDROFLUOROCARBONS AND HYDROCHLOROFLUOROCARBONS

FIELD OF THE INVENTION

The present invention relates to new methods for making hydrofluorocarbons and hydrochlorofluorocarbons.

BACKGROUND OF THE INVENTION

Hydrofluorocarbons (HFCs) and hydrochlorofluorocarbons (HCFCs) are of interest as potential replacements for highly useful chlorofluorocarbons (CFCs). In particular, HFCs are of interest because they do not contain chlorine and therefore do not decompose to form chlorine-containing chemical species, which are suspected of causing depletion of the ozone layer. Both HFCs and HCFCs have been used successfully in place of CFCs as heat transfer agents, blowing agents, and propellants. Thus, HFCs and HCFCs are desirable targets of chemical synthesis.

Applicants believe that known methods for making HFCs and HCFCs, especially methods for making 1,1,1,3,3-pentafluorobutane ("HFC-365"), are highly inefficient, often using disfavored reaction ingredients and/or reaction conditions. For example, U.S. Pat. No. 5,917,098, issued to Bertocchio et al., discloses a process for forming HFC-365 comprising the steps of (a) reacting tetrachloromethane and 2-chloropropene in the presence of a catalyst comprising an amine and a copper salt; and (b) fluorinating with hydrogen fluoride.

The present inventors have come to appreciate that such prior processes are disadvantageous for several reasons. For example, one such disadvantage is that the availability of many halogenated compounds, such as tetrachloromethane and 2-chloropropene, is limited and their use as starting materials tends to be very expensive.

Recognizing this and other drawbacks of the prior art, the present inventors have perceived a need for a new, efficient and more desirable method for producing a wide range of HFCs and HCFCs. These and other objects are achieved by the present invention as described below.

DESCRIPTION OF THE INVENTION AND PREFERRED EMBODIMENTS

The present invention is directed to a method of producing hydrofluorocarbons (HFCs) and/or hydrochlorofluorocarbons (HCFCs) using as a reactant halogenated alkanes, more preferably $C_2$–$C_6$ halogenated alkanes, and even more preferably halogenated alkanes of Formula I, shown below.

Formula I:

$$H_3C—CX_3 \quad (I)$$

wherein X is independently fluorine or chlorine. As used herein with respect to X, the term "independently" means that one X substituent on a compound may differ from another X substituent on the same compound. Accordingly, the X substituents on a compound of Formula I may be all chlorine, all fluorine, or combinations of chlorine and fluorine. Preferably, at least one X is chlorine. Applicants have discovered that halogenated alkanes, and preferably halogenated alkanes in accordance with Formula I, can be used with great advantage in a process which comprises converting the halogenated alkane to an HFC or HCFC.

Applicants have discovered that a process which utilizes such a conversion operation is highly advantageous in that the cost of producing HFCs and HCFCs according to the present halogenated alkane conversion operation is greatly reduced relative to conventional HFC and HCFC production techniques. This reduction in cost is due in part to the relative commercial availability of the present halogenated alkanes in comparison to the starting materials of the prior art.

According to certain preferred embodiments of the present invention, the method of converting a halogenated alkane to an HFC and/or HCFC comprises the step of: (a) reacting a starting halogenated alkane, preferably in accordance with Formula I, with a hydrohalocarbon adduct in the presence of a catalyst to form an addition-reaction product.

According to certain other preferred embodiments of the present invention, the method of converting a halogenated alkane to an HFC and/or an HCFC comprises the steps of: (a) reacting a starting halogenated alkane, preferably in accordance with Formula I, with a hydrohalocarbon adduct in the presence of a catalyst to form an addition-reaction product; and (b) fluorinating said addition-reaction product to produce an HFC and/or an HCFC.

As used herein, the term "hydrohalocarbon adduct" refers generally to alkanes, alkenes and mixtures thereof which are capable of reacting with the starting halogenated alkane to form an addition-reaction product according to the present invention. Preferred hydrohalocarbon adducts include: (1) alkenes described by the Formula (II) below:

$$H_2C=CX_2 \quad (II)$$

wherein X is independently chlorine or fluorine; (2) alkanes of Formula I which are capable of forming alkenes of Formula II in situ in the reaction of the present invention; and (3) mixtures thereof.

Although applicants do not wish to be bound by or to any particular theory of operation, it is believed that the methods according to certain preferred aspects of the present invention involve reaction step (a), and optionally, but preferably, reaction step (b), shown below in Scheme 1.

Scheme 1

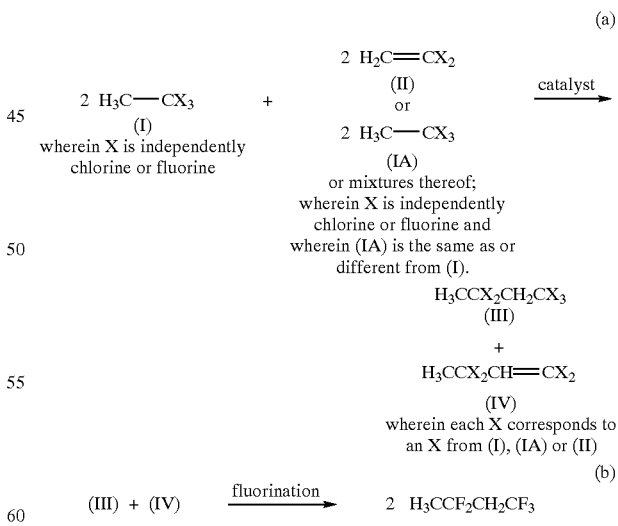

As used herein, the term "addition-reaction product" refers generally to a product comprising either a Formula III alkane or a Formula IV alkene alone, or a mixture of Formula III alkanes and Formula IV alkenes. In certain preferred embodiments of the present invention, the addition-reaction product formed from step (a) may be isolated as a desired end-product HFC and/or HCFC. In such embodiments, further fluorination via step (b) is unnecessary. Examples of Formula III alkanes which can be produced via step (a) include HCFCs, such as, 1-fluoro-1,1,3,3-tetrachlorobutane, 3-fluoro-1,1,1,3-tetrachlorobutane, 1,1-difluoro-3,3,3-trichlorobutane, 1,3-difluoro-1,1,3-trichlorobutane, 3,3-difluoro-1,1,1-trichlorobutane, 3,3-dichloro-1,1,1-trifluorobutane, 1,3-dichloro-1,1,3-trifluorobutane, 1,1-dichloro-1,3,3-trifluorobutane, 3-chloro-1,1,1,3-tetrafluorobutane, 1-chloro-1,1,3,3-tetrafluorobutane, and HFCs, such as, 1,1,1,3,3-pentafluorobutane. Examples of Formula IV alkenes include HCFCs, such as, 1-fluoro-1,3,3-trichlorobut-1-ene, 3-fluoro-1,1,3-trichlorobut-1-ene, 1,1-dichloro-3,3-difluorobut-1-ene, 3,3-dichloro-1,1-difluorobut-1-ene, 1,3-dichloro-1,3-difluorobut-1-ene, 3-chloro-1,1,3-trifluorobut-1-ene, 1-chloro-1,3,3-trifluorobut-1-ene, HFCs, such as, 1,1,3,3-tetrafluorobut-1-ene.

In certain other embodiments of the present invention, the addition-reaction product produced from step (a) is fluorinated via reaction step (b) to form a desired HFC and/or HCFC.

According to certain preferred embodiments of the present invention, reaction step (a) preferably comprises reacting a starting alkane of Formula I with a hydrohalocarbon adduct in the presence of a catalyst under conditions effective to achieve the formation of addition-reaction product at a yield of at least about 50% by mole.

A wide range of starting alkanes in accordance with Formula I are suitable for use in the present invention, including, for example, 1,1-dichloro-1-fluoroethane, 1-chloro-1,1-difluoroethane and 1,1,1-trichloroethane, each of which is commercially available. Furthermore, many compounds of Formula I are known in the literature and are obtainable by art-recognized procedures. Preferred Formula I alkanes include alkanes comprising at least one chlorine group, such as 1,1-dichloro-1-fluoroethane and 1,1,1-trichloroethane.

Any suitable hydrohalocarbon adduct may be used in the method of the present invention. Examples of suitable adducts include: alkenes of Formula II, such as 1-chloro-1-fluoroethene, 1,1-dichloroethene, 1,1-difluoroethene, 1-chloroethene, 1-fluoroethene; alkanes of Formula I, such as those described above; and mixtures thereof. Preferred adducts include 1-chloro-1-fluoroethene, 1,1-dichloroethane, 1,1-dichloro-1-fluoroethane, 1,1,1-trichloroethane and mixtures thereof. More preferred hydrohalocarbon adducts are 1,1-dichloro-1-fluoroethane and 1,1,1-trichloroethane.

In embodiments of the present invention wherein the hydrohalocarbon adduct comprises an alkane of Formula I, the alkane adduct may be the same as or different from the starting alkane of Formula I. In certain preferred embodiments, the hydrohalocarbon adduct comprises the same compound as the starting alkane.

Any suitable amounts of starting alkane and hydrohalocarbon adduct can be used in the present invention. Preferably, the amount of such materials used is an amount effective to achieve a greater than 30% conversion (on a mole basis) of the starting alkane to an addition-reaction product. As will be recognized by those of skill in the art, the reactants are generally present in approximately equimolar amounts unless one reactant is more volatile or less stable in which case it may be used in excess. Accordingly, the mole ratio of starting alkane to hydrohalocarbon adduct is preferably from about 3:1 to about 1:1, more preferably from about 2:1 to about 1:1 and even more preferably about 1:1.

Any of a wide range of known catalysts are suitable for use in the present invention. Examples of suitable catalysts include Lewis acids, derivatives of Lewis acids, and the like. Preferred catalysts include Lewis acid catalysts such as: boron trifluoride; aluminum compounds of the formula: $AlCl_nF_{3-n}$, wherein n=0 to 3, such as aluminum trichloride; boron compounds of the formula: $(C_6F_5)_3B$ (wherein B is boron); tin tetrachloride; titanium tetrachloride; antimony trichloride and the like. Preferred Lewis acids agents include aluminum compounds of the formula: $AlCl_nF_{3-n}$, wherein n=0 to 3. A particularly preferred Lewis acids comprises aluminum trichloride.

Those skilled in the art will appreciate that the amount of catalyst to be used according to the present invention will depend on many variables, including the particular starting materials being used and the desired yield from the reaction step (a). For example, although applicants do not wish to be bound by or to any theory of operation, it is believed that a relatively large amount of catalyst promotes undesirable polymerization of reaction intermediates, thus lowering the yield of desired product. As shown below in Scheme 2, it is believed that two different intermediates ($I_a$ and $I_b$) may be formed from the starting alkane in the reaction of the present invention.

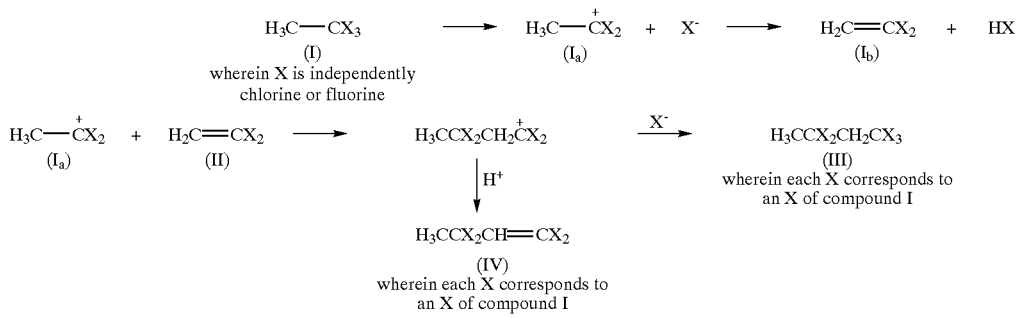

It is believed that when two or more alkenes come in contact with each other in solution, they tend to polymerize. Such polymerization reduces the amount of alkene available in solution for reaction with intermediate ($I_a$) and consequently reduces the desired product yield. However, by limiting the amount of catalyst used, the conversion of starting alkane to alkene $I_b$ can be hindered such that the formation of intermediate $I_a$ predominates alkene $I_b$ formation. Accordingly, each alkene in solution is more likely to encounter and react with an intermediate $I_a$ to form desired product rather than polymerize with another alkene.

Preferably, the amount of catalyst used is an amount effective to achieve a greater than 30% conversion (on a mole basis) of the starting alkane to an addition-reaction product. For preferred processes in which the starting alkane and hydrohalocarbon adduct are 1,1-dichloro-1-fluoroethane and the catalyst is a Lewis acid, the mole ratio of Lewis acid catalyst to 1,1-dichloro-1-fluoroethane is less than about 1:2, preferably less than about 1:3, and more preferably less than about 1:4. In light of the above disclosure, those of skill in the art will be readily able to determine an amount of catalyst suitable for use in the present invention without undue experimentation.

The temperature at which the reaction step (a) is conducted and the period of reaction will depend in part on the starting materials and the desired yield. Generally, it is preferred that the reaction temperature be controlled so as to hinder alkene polymerization. The reaction temperature for step (a) is preferably maintained at less than about 120° C., more preferably at less than about 100° C. and even more preferably at leass than about 90° C. It is contemplated that in certain embodiments in which polymerization of the alkenes of Formula II is considered to be especially detrimental, the reaction temperature is preferably maintained at less than about 80° C. In many preferred embodiments of the present invention, the temperature of reaction step (a) is maintained at from about 20° C. to about 120° C. In view of the present teachings, those skilled in the art will be able to adapt the reaction parameters to achieve the particular desired results for numerous starting materials and desired HFCs.

As an optional step, the addition-reaction product produced from step (a) may be purified by conventional means, such as, for example, distillation. Optionally, but preferably, unreacted starting materials recovered from such a purification step are recycled for further reaction. Recycling such unreacted starting material generally results in higher overall yields and selectivity of the reaction step (a).

As mentioned above, certain preferred embodiments of the present invention comprise the step of fluorinating the addition-reaction product to form an HFC. The fluorination step preferably comprises reacting the addition-reaction product with a fluorinating agent in the presence of a fluorination catalyst to produce an HFC in a yield of about 80% by mole.

In general, suitable fluorination agents include any material capable of providing fluorine to the reaction. Examples of suitable fluorinating agents are substantially anhydrous hydrogen fluoride, aqueous hydrogen fluoride, metal fluorides, halogen fluorides, elemental fluorine and sulfur fluorides. A preferred fluorination agent is substantially anhydrous hydrogen fluoride (HF). Anhydrous hydrogen fluoride is preferred because the presence of water in the reaction tends to deactivate the fluorination catalyst. The term "substantially anhydrous", as used herein, means that the HF contains less than about 0.05 weight percent water and preferably contains less than about 0.02 weight percent water. It should be understood, however, that the presence of water in the catalyst can be compensated for by increasing the amount of catalyst used.

The fluorination catalyst preferably comprises an inorganic metal catalyst which promotes a reaction involving the addition of fluorine for chlorine in a chlorinated organic molecule. Numerous fluorination catalysts are known to those skilled in the art. Exemplary catalysts include, without limitation, chromium, copper, aluminum, cobalt, magnesium, manganese, antimony, tantalum, niobium, titanium, tin, zinc, nickel and iron oxides, hydroxides, halides, oxyhalides and inorganic salts thereof, Cr2O3/Al2O3, Cr2O3/AlF3, Cr2O3/carbon, CoCl2CrO3/Al2O3, NiCl2/Cr2O3/Al2O3, CoCl2AlF3 and NiCl2/AlF3. Additionally, supported metal catalysts such as nickel, cobalt, zinc, iron, and copper supported on chromia, magnesia, or alumina may be used. Such chromium oxide/aluminum oxide catalysts are known and are described, for example, in U.S. Pat. No. 5,155,082, which is incorporated herein by reference. Preferably, chromium oxide ($Cr_2O_3$), a commercially available catalyst, is used.

Any suitable amounts of fluorinating agent and fluorination catalyst can be used in the present invention. Preferably, the amount of fluorinating agent used is an amount effective to achieve a greater than 90% conversion of addition-reaction product to HFC. For example, in particularly preferred embodiments in which the addition-reaction product comprises a mixture of 1,1,3-trichloro-1,3-difluorobutane and 1,3-dichloro-1,3-difluorobut-1-ene and the HFC comprises HFC-365, the mole ratio of addition-reaction product to HF is preferably about 1:30, more preferably about 1:25, and even more preferably about 1:20.

The amount of catalyst used can vary widely and can be determined by one skilled in the art without undue experimentation. The amount depends on a number of factors including the catalyst employed, reactants and other process variables. In a batch process, the mole ratio of addition-reaction product to catalyst used is preferably greater than about 2:1, more preferably greater than about 3:1, and even more preferably greater about 4:1.

According to the present invention, the fluorination reaction may comprise a liquid-phase or vapor-phase reaction. Generally, in the liquid-phase, the fluorination reaction comprises combining the addition-reaction product, fluorinating agent and fluorination catalyst under pressure to produce an HFC.

The temperature at which the liquid-state fluorination reaction is conducted and the period of reaction will depend on the starting materials, amounts used, and catalyst used. In view of the present teachings, those skilled in the art will be able to adapt the reaction parameters to achieve the particular desired results for numerous starting materials and desired HFCs. For methods involving the use of a mixture of 1,1,3-trichloro-1,3-difluorobutane and 1,3-dichloro-1,3-difluorobut-1-ene as the addition-reaction product, temperatures are preferably from about 10° C. to about 100° C., more preferably from about 20° C. to about 40° C., and even more preferably from about 25° C. to about 35° C. Furthermore, pressures are preferably from about 0 to about 300 psig, more preferably from about 0 to about 200 psig, and even more preferably from about 0 to about 175 psig.

Vapor-phase fluorination reactions according to the present invention are preferably carried out in a reactor vessel. One or more of the reactants comprising the fluorination agent and the addition-reaction product may be preheated in at least one vaporizer before feeding the reactor. Suitable temperatures for preheating range from about 20° C. to about 400° C., preferably from about 30° C. to about 350° C., and more preferably from about 50° C. to about 300° C.

The fluorination reactor is charged preferably with a fluorination catalyst before feeding the reactants to the reactor.

Before adding the reactants to the fluorination reactor, it may be preferable to pretreat the catalyst chemically and/or physically to create active sites which facilitate fluorination.

For example, the catalyst can be pretreated by calcining it under a flow of inert gas, such as nitrogen, at a temperature comparable to or higher than that of the fluorination reaction. Next, the calcined catalyst is exposed to a fluorinating agent alone or in combination with up to about 5 to about 99 weight percent of inert gas at a temperature from about 25° C. to about 450° C. for at least about an hour.

The reactants can be fed individually or as a mixture to the reactor, or diluted with inert material, such as nitrogen or argon, or perhalogenated material. Once the reaction is underway, the reactants may be continuously added under pressure to supply the additional amounts of reactants needed to continue the process.

The temperature at which the vapor-phase fluorination reaction is conducted and the period of reaction will depend on the starting materials, amounts used, and catalyst used. In view of the present teachings, those skilled in the art will be able to adapt the reaction parameters to achieve the particular desired results for numerous starting materials and desired HFCs. For methods involving the use of a mixture of 1,1,3-trichloro-1,3-difluorobutane and 1,3-dichloro-1,3-difluorobut-1-ene as the addition-reaction product, temperatures in the fluorination reactor are preferably from about 100° C. and about 400° C., more preferably from about 150° C. to about 350° C., and even more preferably from about 200° C. to about 350° C. Pressure is not critical. Atmospheric, sub- or super-atmospheric pressures can be used.

In a continuous process, the contact time for the reactants stream is preferably from about 1 to about 240 seconds, more preferably from about 1 to about 200 seconds, and even more preferably from about 1 to about 120 seconds.

In many embodiments, the HFC product produced in the fluorination reaction will comprise not only HFC's, but also by-products and impurities. As an optional step, at least a portion of the HFC may be purified via conventional means, such as distillation, phase separation, HF-extraction, or water scrubbing. As a further optional step, any addition-reaction product recovered from the fluorination reaction may be recycled back to the reactor for further fluorination.

EXAMPLES

In order to illustrate, in a non-limiting manner, the present invention is described in connection with the following examples.

Example 1

This example illustrates the synthesis of 1,1,3-trichloro-1,3-difluorobutane and 1,3-dichloro-1,3-difluorobut-1-ene using 1,1-dichloro-1-fluoroethane as both the starting halogenated alkane of Formula I and the hydrohalocarbon adduct.

To a 1 liter autoclave, equipped with a vent condenser, is charged 10 grams of aluminum chloride. Subsequently, 200 grams of 1,1-dichloro-1-fluoroethane are charged to the autoclave and the autoclave is heated to 100° C. with the vent condenser set to 200 psig pressure. The mixture is stirred for 12 hours. The reaction mixture is then poured into an ice water solution. The organic compounds are phase separated. Gas chromatography shows that the reaction product is 25% 1,1,3-trichloro-1,3-difluorobutane and 25% 1,3-dichloro-1,3-difluorobut-1-ene. The remainder of the product substantially comprises unreacted 1,1-dichloro-1-fluoroethane.

Example 2

This example illustrates the synthesis of 1,1,1,3,3-pentafluorobutane from a mixture of 1,1,3-trichloro-1,3-difluorobutane and 1,3-dichloro-1,3-difluorobut-1-ene.

To a 1 liter autoclave is charged about 25 grams of $SbCl_5$ and 50 grams of a mixture of 1,1,3-trichloro-1,3-difluorobutane and 1,3-dichloro-1,3-difluorobut-1-ene. The autoclave is cooled to 0° C. and 150 grams of anhydrous HF is charged. The autoclave is warmed slowly to 100° C., while the pressure is maintained below 400 psig. The mixture is stirred for 12 hours. The reaction mixture is worked up using water and caustic solutions. 1,1,1,3,3-pentafluorobutane is recovered in 90% yield (based on molar basis of starting alkane/alkene mixture).

Having thus described a few particular embodiments of the invention, various alterations, modifications and improvements will readily occur to those skilled in the art. Such alterations, modifications and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. A method for the preparation of a hydrofluorocarbon comprising the steps of:

(a) reacting a starting halogenated alkane corresponding to the formula (I):

$$H_3C\text{—}CX_3 \tag{I}$$

wherein X is independently fluorine or chlorine, with a hydrohalocarbon adduct, said hydrohalocarbon adduct comprising a halogenated alkane which is the same or different from said starting halogenated alkane, in the presence of a catalyst to form an addition-reaction product; and (b) fluorinating said addition-reaction product to produce a hydrofluorocarbon.

2. The method of claim 1 wherein at least one X of said starting halogenated alkane is chlorine.

3. The method of claim 2 wherein said starting halogenated alkane is 1,1,1-trichloroethane, 1,1-dichloro-1-fluoroethane or 1-chloro-1,1-difluoroethane.

4. The method of claim 3, wherein said starting halogenated alkane is 1,1-dichloro-1-fluoroethane.

5. The method of claim 1 wherein said hydrohalocarbon adduct comprises an alkane of Formula I.

6. The method of claim 5 wherein said hydrohalocarbon adduct alkane is 1,1,1-trichloroethane, 1,1-dichloro-1-fluoroethane, 1-chloro-1,1-difluoroethane or a mixture of two or more of these.

7. The method of claim 5 wherein said alkane of said hydrohalocarbon adduct is the same compound as said starting halogenated alkane.

8. The method of claim 1 wherein said hydrohalocarbon adduct further comprises an alkene described by the formula II:

$$H_2C\text{=}CX_2 \tag{II}$$

wherein X is independently chlorine or fluorine.

9. The method of claim 8 wherein said alkene of Formula II is 1-chloro-1-fluoroethene, 1,1-dichloroethene or a mixture thereof.

10. The method of claim 1 wherein said hydrohalocarbon adduct comprises a mixture of at least one alkane of Formula I and at least one alkene of Formula II.

11. The method of claim 10 wherein said at least one alkane comprises 1,1-dichloro-1-fluoroethane.

12. The method of claim 10 wherein said at least one alkene comprises 1-chloro-1-fluoroethene.

13. The method of claim 1 wherein said catalyst is a Lewis acid catalyst.

14. The method of claim 13 wherein said Lewis acid is selected from the group consisting of aluminum trichloride; boron trifluoride; aluminum compounds of the formula: AlClnF3-n; boron compounds of the formula: $(C_6F_5)_3B$; tin tetrachloride; titanium tetrachloride; antimony trichloride; and mixtures of two or more of these.

15. The method of claim 14 wherein the mole ratio of Lewis acid catalyst to starting halogenated alkane and hydrohalocarbon adduct is less than 1:2.

16. The method of claim 15 wherein the mole ratio of Lewis acid catalyst to starting halogenated alkane and hydrohalocarbon adduct is less than 1:4.

17. The method of claim 1 wherein said reacting step (a) is conducted at a temperature of less than about 100° C.

18. The method of claim 17 wherein said reacting step (a) is conducted at a temperature of less than about 90° C.

19. The method of claim 1 wherein said fluorinating step (b) comprises reacting the addition-reaction product with a fluorinating agent in the presence of a fluorination catalyst to form an HFC.

20. The method of claim 19 wherein said fluorinating agent is selected from the group consisting of substantially anhydrous hydrogen fluoride, aqueous hydrogen fluoride, metal fluorides, halogen fluorides, elemental fluorine, sulfur fluorides and mixtures of two or more of these.

21. The method of claim 20 wherein said fluorinating agent is substantially anhydrous hydrogen fluoride.

22. The method of claim 21 wherein the mole ratio of addition reaction product to catalyst is greater than 4:1.

23. The method of claim 1 wherein said fluorinating step (b) comprises a liquid-phase reaction.

24. The method of claim 1 wherein said fluorinating step (b) comprises a vapor-phase reaction.

25. The method of claim 24 wherein the fluorination step (b) produces a product stream comprising HFCs.

26. A method for the preparation of a hydrofluorocarbon comprising the steps of:

(a) reacting a starting halogenated alkane corresponding to the formula (I):

$$H_3C-CX_3 \qquad (I)$$

wherein X is independently fluorine or chlorine, with a hydrohalocarbon adduct, each of said starting halogenated alkane and said hydrohalocarbon adduct comprising 1,1-dichloro-1-fluoroethane, in the presence of a Lewis acid to produce an addition-reaction product comprising a mixture of 1,1,3-trichloro-1,3-difluorobutane and 1,3-dichloro-1,3-difluorobut-1-ene; and (b) fluorinating said addition-reaction product to produce 1,1,1,3,3-pentafluorobutane.

* * * * *